United States Patent [19]

Sportoletti et al.

[11] Patent Number: 4,717,719

[45] Date of Patent: Jan. 5, 1988

[54] MODIFIED GLUCOSAMINOGLUCANS HAVING ANTITHROMBOTIC ACTIVITY

[75] Inventors: Giancarlo Sportoletti; Piergiuseppe Pagella; Pietro Cremonesi, all of Milan, Italy

[73] Assignee: Italfarmaco S.p.A., Milan, Italy

[21] Appl. No.: 572,448

[22] Filed: Jan. 20, 1984

[30] Foreign Application Priority Data

Oct. 25, 1983 [IT] Italy ............................ 23422 A/83

[51] Int. Cl.$^4$ ............................................ A61K 31/725
[52] U.S. Cl. .................................... 514/56; 514/822; 514/824
[58] Field of Search ...................... 424/183; 536/21; 514/56, 822, 824

[56] References Cited

U.S. PATENT DOCUMENTS

| | | | |
|---|---|---|---|
| 3,118,816 | 1/1964 | Cushing | 536/21 |
| 4,351,938 | 9/1982 | Barnett | 536/21 |
| 4,385,046 | 5/1983 | Milbrath et al. | 424/1 |
| 4,401,662 | 8/1983 | Lormeau et al. | 424/183 |

FOREIGN PATENT DOCUMENTS

| | | | |
|---|---|---|---|
| 1201322 | 9/1965 | Fed. Rep. of Germany | 536/21 |
| 8101004 | 4/1981 | PCT Int'l Appl. | 424/183 |
| 2078768 | 1/1982 | United Kingdom | 536/21 |

OTHER PUBLICATIONS

Holmer et al., Anticoagulant and Antithrombotic Effects of Heparin and Low Molecular Weight Heparin Fragments in Rabbits, Thrombosis Research 25, pp. 475–485 (1982).
Wolfrom et al., Acetylative Desulfation of Carbohydrate Acid Sulfates, J. Am. Chem. Soc. 72, pp. 2859–2861 (1950).
Hirano et al., Some N-Acyl Derivatives of N-Desulphated Heparin, Carbohydrate Research 59, pp. 285–288 (1977).
Long et al., Effects of Heparin, de-N-sulfated Heparin and de-N-sulfated N-acetylated Heparin on . . . Inhibition of Factors Xa and on . . . Inhibition of Thrombin, Chem. Abs. 98:158403s (1983).
Halfarmaco S.p.A., Modified Glycosaminoglycans with Antilipemic Activity Having No Anticoagulatory Effect and Pharmaceutical Preparations . . . , Chem. Abs. 96:104693b (1981).
Nagasawa et al., Studies of the Influence of N-Substitution in Heparin on its Anticoagulant Activity, Chem. Abstracts 87:62618n (1977).
Thrombosis and Cardiovascular Diseases, Edited by Antonio Strano, Plenum Press, New York and London.
Goodman and Gilman's, "The Pharmacological Basis of Therapeutics" 7th Edition, Macmillan Publishing Co., N.Y., Copyright 1985.
"Platelets in Biology and Pathology" Editor, J. L. Gordon, Cambridge, 1976.
"The Thrombin" vol. 1, Editor, Raymond Machovich, M.D., PhD., D.Sc., 1984.
"The Thrombin" vol. II, Editor, Raymond Machovich, M.D., PhD., D.Sc., 1984.
"Principles of Biochemistry" 6th Edition, by Doctors, White, Handler, Smith, Hill and Lehman, 1973.
"Thrombis Research" vol. 8, pp. 413–416, 1976, Brief Communication.

*Primary Examiner*—J. R. Brown
*Assistant Examiner*—John W. Rollins, Jr.
*Attorney, Agent, or Firm*—Bucknam and Archer

[57] ABSTRACT

Pharmaceutical compositions are described which have antithrombotic activity suitable for the prevention and for the therapy of cardiac infarcts, cerebral infarcts and venous thrombosis. They contain as the active component a fraction of heparin which has been modified by nitrogen desulfatation and succinylation, which fraction contains less than 10% of the N-sulfate groups of the heparin starting material and more than 0.6 succinyl radicals per disaccharide unit. The method of treatment is described.

1 Claim, No Drawings

MODIFIED GLUCOSAMINOGLUCANS HAVING ANTITHROMBOTIC ACTIVITY

The present invention relates to pharmaceutical compositions containing as the active components modified glucosaminoglucans as antithrombotic agents.

The thrombus is an aggregate of platelets and polymorphonuclear leukocytes in a fibrin net and is considered the crucial element causing very serious pathological conditions such as the vascular lesions which are known as cardiac infarct, cerebral infarct and venous thrombosis.

It is necessary to stress that the thrombus is structurally different from the coagulum called "hemostatic plug" or "clot". In fact, while the latter is formed in the locus of the vascular lesion, the real thrombus is formed also in the circulation and does not necessarily follow a vascular lesion. The confusion between these aggregates has caused for a long time the erroneous belief that a simple alteration of the coagulative system due to hypercoagulability forms the thrombus and, therefore, has caused people to believe that this phenomenon may be foreseen or may be cured merely by the administration of anticoagulants. Further, it is necessary to distinguish between Arterial Thrombosis and Venous Thrombosis for the consequences of the formation of the thrombus itself in the arteries where the stasis of the hematic flow with subsequent production of the infarct occurs and in the veins in which the rupture or the lengthening of the thrombus and its embolization at the lungs level are the principal causes of death.

In the profilaxis of thrombosis there are used substances with an antiaggregating activity for the platelets as well as fibrinolytic agents which decompose the fibrin into soluble peptides as well as agents which operate as inhibitors of the factor or factors which lead to the network of fibrin. Among these factors, thrombin and the factor Xa ("activated factor X") which are components of the mechanism of intrinsic coagulation have been identified. One of the most widely utilized inhibitors of these two factors is heparin.

The antithrombotic activity of this drug, in general, is expressed in terms of anti-Xa activity in the sense that the greater is its specific value, the greater is the antithrombotic activity. Actually, the commercial preparations of heparin exhibit a high anti-Xa activity associated with a high anticoagulant activity, the latter in general being expressed in international units per mg(I.U./mg). This fact causes side effects which are not insignificant, such as the formation of hematoma in the locus of the inoculation, dangerous conditions of hypocoagulability when the preparations are used for an extensive period of time.

In addition, as it has been demonstrated by clinical studies carried out up to the present time, the prevention of Venous Thrombosis may be achieved while the data with respect to Arterial Thrombosis are conflicting.

Therefore, the use of a pharmaceutical drug which presents low or zero anticoagulant and anti-Xa activities and eventually also a certain fibrinolytic activity would be very desirable in the prevention of both Venous as well as Arterial Thrombosis. For this reason, research is being carried out throughout the world towards the preparation of heparin fractions (obtained from heparin in toto which exhibits a significant polydispersion of molecular weight with or without structural variations) which exhibit high anti-Xa activity and reduced anticoagulant activity, see for instance, Holmer E. et al. Thrombos, Res., V:25,475, 1982.

It has now been found surprisingly that the derivatives described in Italian Patent Application No. 22851 A/80, that is heparin derivatives obtained by a suitable process of N-desulfatation and subsequent succinylation exhibit very low or no anticoagulant activity, reduced or no anti-Xa activity while still exhibiting a satisfactory residual lipasemic activity with respect to the heparin starting material and that they exhibit in vivo a significant inhibitory activity in the formation of the thrombus as described in the examples reported hereinbelow which, however, are not intended to limit the invention.

This activity cannot be explained in intensity on the basis of the residual values (nil or essentially so) of both the anticoagulant activity as well as the anti-Xa activity exhibited by the compounds(0.2 I.U./mg. and 2 U./mg., respectively).

It is an object of the present invention to provide compounds which exhibits the ability to protect against the formation of the thrombus exhibited by the other substances, a fact which is surprising and in contrast with the state of the art In addition to the ability of inhibiting the formation of the thrombus as mentioned hereinabove, the compound according to the present invention exhibits a certain fibrinolytic activity which is shown, as it will be described in more detail hereinbelow, in rats in vivo by means of the determination of the F. D. P. (Fibrin Degradation Products), the period for the lysis of the euglobulins and in man by means of the latter test.

Succinyl derivatives of N-desulfated heparin have also been described in German No. 1,201,322 of Roussel-Uclaf. However, in this patent, only the antilipemic activity of the same substances is described, which activity is accompanied by a low anticoagulant activity.

As an alternative, one could postulate a common mechanism of antithrombosis for the commercial preparations of heparin and succinyl derivative in conflict with the hypothesis that the antithrombotic activity is necessarily connected with an inhibition of the factor Xa, a theory which up to now has been followed by many investigators. This would lead to an hypothesis that the mechanism consists of a release from the vascular wall of a factor which is not well known in an amount sufficient to interfere with the aggregation of the platelets and/or with the formation of fibrin.

In addition to the inhibitory activity of the formation of the thrombus discussed hereinabove, the product exhibits certain fibrinolytic activity demonostrated as it will be described hereinbelow by tests in rats in vivo through the evaluation of F. D. P. (Fibrin Degradation Products), the time of lysis of the euglobulins and in men by means of the latter test.

The N-desulfated and succinylated glucosaminoglucans derivatives which are used as the active components in the compositions according to the present invention are obtained as already mentioned hereinabove according to Italian Patent Application No. 22851 A/80 and in particular, by hydrolyzing heparin at a temperature preferably between 70° and 100° C. for a period of time greater than three hours with a strong acid of at least 0.1 normality (0.1 N) and preferably equal to or higher than 0.5N and then succinylating the hydrolysis product so obtained by reaction with succinic anhydride at a pH higher than 7, the ratio by weight between succinic anhydride and hydrolyzed heparin being between 1:1 and 5:1.

In particular, the glucosaminoglucan derivatives being used in the compositions according to the invention contain less than 10% of the N-sulfate groups present in the heparin starting material and more than 0.6 succinyl residues, preferably about 1.2 succinyl residues per disaccharide unit.

Preparation

In a 3 liter flask provided with condenser mechanical stirrer and an inlet for nitrogen so as to operate in an inert atmosphere, are placed two liters of distilled water and 200 grams of the sodium salt of heparin. The product is dissolved at room temperature under stirring and then 400 cc of 2N HCl are added. The clear solution is deaerated by means of nitrogen and while keeping a nitrogen atmosphere, the solution is placed on a boiling water bath and kept in these conditions for a period of 6 hours. The solution is then cooled to room temperature and while cooling with ice, the pH is brought to 8.5 by the addition of a cold saturated solution of NaOH. While keeping the temperature at the initial range of 5°–10° C. and the pH at about 8 by the addition of a solution of NaOH, 400 grams of succinic anhydride are added in portions. The final addition brings the pH to about 7.4–7.5. The cold solution is kept stirring for 30 minutes and then three volumes of 95° ethanol are added. The precipitate which is formed, which initially is oily, but after standing becomes a solid, is filtered under suction and air-dried. The precipitate is redissolved in three liters of distilled water and dialized in a dialyzer of nominal cut-off, 600 daltons, against distilled water up to the elimination of sodium succinate. The final solution is then lyophilized. The product, 200 grams, is obtained in the form of needles.

R.M.N. Spectrum $^{13}$C of G.G.M.

The data have been obtained with 25.2 MHZ in dioxane-D$_2$O; internal standard dioxane, (p.p.m. 67.4); the data are reported in p.p.m. The method used has been reported by G. Gatti, B. Casu, G. K. Hamer and A. S. Perlin, Macromolecules 12, 1001 (1979).

The spectrum compared with the spectrum of the sodium salt of heparin, determined under the same conditions, gives the following signals and differences:

(1) A new signal is noted at 181.8 attributable to the COO$^-$ of the succinic residue;

(2) A new signal at 177 attributable to the —CONH of the succinic residue;

(3) A signal at 176.7 attributable to the COOH of the iduronic residue equal to that of heparin;

(4) A small signal at 102 attributable to the C$_1$ of small quantities of the residue of glucuronic acid, equal to that of heparin;

(5) A signal at 100 attributable to the C$_1$ of the iduronic acid residue equal to that of heparin;

(6) A new signal at 95.3 attributable to the C$_1$ of the unit of N-succinyl-glucosamine. In a similar manner, the disappearance of the signal at 97.7 is noted, which signal is attributable to the C$_1$ of the residue of glucosamine N-sulfate which is characteristic of the heparin starting material;

(7) A new series of signals between 72 and 76, attributable to C$_2$ and C$_4$ of the N-succinylglucosaminic residue and to the C$_2$ of the iduronic residue, these signals in the spectrum of heparin are gathered in a sole intense signal at 76;

(8) A pair of signals at 70 and 71 attributable to C$_3$ and C$_5$ of the N-succinylglucosaminic residue and to C$_3$ and C$_5$ of the iduronic residue equal to the signals of the same atoms of heparin;

(9) A signal at 67 attributable to C$_6$ of the N-succinylglucosaminic residue equal to the signal of C$_6$ of the N-sulfonyl residue of heparin;

(10) A new signal at 54.5 attributable to C$_2$ of N-succinylglucosaminic residue. At the same time, there is noted the disappearance of the signal at 58.8 which is due to the C$_2$ of N-sulfonylglucosaminic residue in the heparin spectrum;

(11) Two new signals at 33.0 and 33.5 attributable to —CH$_2$COO$^-$ and —CH$_2$—CO—NH— of the succinic residue in N-succinyl heparin.

(1) ANTITHROMBOTIC ACTIVITY

1.1 Determination of Activity

The model being used is commonly known as the model of Umetzo (Teruhiro Umetzo et al - Thrombosis and Haemostasis - Stuttg. -v.39, 74, 1978). This model consists of creating in rats a shunt between the right carotid and the left jugular vein by means of a silicon tube in the interior of which is placed a thread of ethicon which is wound silk. Due to its presence in the hematic flow which has been subjected to the shunt, one creates around the thread a thrombus which results the highest in weight in the absence of antithrombotic agents and which is more or less reduced or completely eliminated in the presence of the antithrombotic agents according to the specific potency and the dosage.

As a reference point, heparin (Internal Standard: 155 I.U./mg of anticoagulant and 168 U./mg of Anti-Xa activity determined according to the colorimetric test Hepachrom X Stago-Diagnostic Stago, Paris, France) is used.

The product tested is referred hereinbelow as GGM: the sodium salt of partially N-desulfated succinyl glucosaminoglucan having anticoagulant activity 0.2 I.U./mg and 2 U./mg of anti-Xa activity determined as mentioned hereinabove for heparins obtained as described in Italian Patent Application No. 22851 A/80 using the same standard heparin as the starting material.

There are used for the tests male albino Wistar rats, of about 350 g weight anesthesized by urethan (1.25 g/kg b.w. i.p.).

Extraneous material in the extracorporeal circulation: Ethicon i.d. 2.5 mm of 6 mg weight.

The product being tested or the standard were injected through the shunt immediately prior to the inception of the extracorporeal circulation in the volume of 1 mg/kg b.w. of physiological solution. The duration of the extracorporeal circulation was 15 minutes.

The thrombus was weighed immediately after removal of the silk thread from the shunt so that the correct weight of the thrombus was determined by subtracting the weight of the thread from the total weight.

One group of animals were treated only with physiological solution with respect to the volume of administration, 1 ml/kg b.w. for the purpose of obtaining the average value of the weight of the thrombus in the absence of inhibitory substances. In each animal treated there was determined the time of coagulation which was taken as the parameter of the influence of the treatment on the coagulatine system.

The results so obtained are reported in Table 1 hereinbelow:

TABLE 1

| Treatment (mg/kg) | Variation %(*) Thrombosis Formation | Effective Dose 50 (DE 50: mg/kg) |
|---|---|---|
| Physiological | — | |
| Heparin 0.062 | 29 | 0.14 |
| Heparin 0.125 | 43 | |
| Heparin 0.250 | 67 | |
| Heparin 0.500 | 88 | |
| Heparin 1.000 | 94 | |
| GGM 12.50 | 29 | 28.95 |
| GGM 25.00 | 47 | |
| GGM 50.00 | 69 | |
| GGM 100.00 | 74 | |
| GGM 200.00 | 82 | |
| GGM 400.00 | 89 | |

(*) The percent inhibition of the formation of the thrombus is calculated in terms of the decrease in weight of the thrombus obtained compared with the weight obtained after the administration only of the physiological solution. The average value of the weight of the thrombus obtained after administration of the physiological solution (average value of 30 experiments):101.93 +— 6.38 mg.
Period of time to achieve coagulation: the period of time to cause coagulation after administration of the physiological solution resulted as an average 144.14 +— 6.21 seconds. After treatment with heparin, it varied in a manner dependent on the dose up to reaching the value of 521.40 +— 41.06 in the dose of 1 mg/kg. However, after administration of GGM in the dose up to 200 mg/kg, the value remained around the basal value to reach the value of 228.50 +— 17.55 seconds in the dose of 400 mg/kg b.w.

The data reported hereinabove clearly show that the antithrombotic activity of GGM is not connected with the anticoagulant activity in terms of activation of antithrombin. Further, in view of the low specific value in terms of anti-Xa activity, the antithrombotic activity of GGM cannot be attributed to a direct activity of inhibition of the Xa factor.

1.2 Duration of the Activity

Under the same working conditions described in the preceding example, rats in groups of six animals each, were administered heparin in the dose of 77.5 I.U./kg b.w. and GGM in the dose of 115 mg/kg p.c. in doses equally active in terms of antithrombotic activity at the beginning of the experiment and then irregular period of time prior to the beginning of the extracoporeal circulation as indicated in Table 2. In the same table are reported data of percent of inhibition obtained after different periods of time.

TABLE 2

| Initial Period of Extracorporeal Circulation After Intravenous Treatment in Minutes | Percent Inhibition of the Thrombus After Intravenous Administration (*) | |
|---|---|---|
| | Heparin | GGM |
| 15 | 86.8 | 72.4 |
| 45 | 57.8 | 61.3 |
| 75 | 18.5 | 36.7 |
| 135 | — | 16.1 |

(*) Average weight of the thrombus in animals treated only with physiological solution, that is control animals 92.98 +— 5.69 mg

(2) FIBRINOLYTIC ACTIVITY

2.1 In Rats

2.1.1 F. D. P. in rats in vivo, after intravenous administration

Wistar male rats of average weight about 220 g were used. The administration was carried out intravenously in the animals while awake at intervals of 30 minutes, 60 minutes, 120 minutes and 240 minutes prior to killing the animals. As the carrier, distilled water was used in the amount of 1 cc/kg. The fibrin degradation products were determined on the plasma utilizing the kit of Boehringer Mannheim, Staphylococcal Clumping Test. The basal value was determined after administration of the physiological solution in the amount of 1 cc/kg b.w. The results are reported in Table 3.

TABLE 3

| Group | F.D.P. In $\mu g/cc$ Time Interval | | | | |
|---|---|---|---|---|---|
| | 0' | 30' | 60' | 120' | 140' |
| Physiological solution | 0.250 | 0.400 | 0.268 | 0.351 | 0.555 |
| GGM 1 mg/kg | — | 0.527 | 0.541 | 0.562 | 0.530 |
| GGM 10 mg/kg | — | 1.000 | 1.138 | 0.968 | 0.609 |
| GGM 30 mg/kg | — | 1.500 | 1.475 | 0.612 | 0.625 |
| GGM 100 mg/kg | — | 0.350 | 0.625 | 4.425 | 1.262 |

2.1.2 Period of Time for the Lysis of Euglobulins

The criterion used is as follows: the euglobulin fraction of the plasma contains the activator of the plasminogen, the plasminogen and fibrinogen. The fraction containing the euglobulins is coagulated by means of thrombin and the period of time interval required for the subsequent lysis of the coagulum is determined in the presence or the absence of GGM. Three levels of doses in the plasma of Wistar rats were tested utilizing the kit Euglobulin The tested doses were 25.50 and 100 $\mu g$ of GGM with properties equal to the product used hereinabove. The results obtained are reported in Table 4.

TABLE 4

| Dose ($\mu g$) | Period of Time for the Lysis of the coagulum (*) (in minutes) | Variation % Relative to the Control |
|---|---|---|
| GGM 25 $\mu g$ | 18' | −35 |
| Control | 28' | |
| GGM 50 $\mu g$ | 18' | −38 |
| Control | 29' | |
| GGM 100 $\mu g$ | 28' | −42 |
| Control | 48' | |

3. IN HUMANS

3.1 Period of time for the lysis of the euglobulins

Human plasma obtained from healthy volunteer individuals was used. The test was carried out on plasma utilizing Euglobulin Lysis Reagent kits of Dade Diagnostic-Aguada, Puerto Rico. The doses of 25, 50 and 100 $\mu g$ of GGM with the properties equal to the properties of the product used in the preceding examples were tested. The results obtained are reported in Table 5.

TABLE 5

| Dose | Time Interval for the Lysis of the Coagulum (*) (in minutes) | Variation % relative to the Control |
|---|---|---|
| GGM 25 $\mu g$ | 400 | −13% |
| Control | 459 | |
| GGM 50 $\mu g$ | 100 | −78% |
| Control | 460 | |
| GGM 100 $\mu g$ | 190 | −59% |
| Control | 470 | |

(*) Average value obtained for each dose on volunteer individuals

The present invention relates to all the industrial aspects connected with the use of glucosaminoglucan derivatives as antithrombotic agents and in particular pharmaceutical compositions containing as the active principle a predetermined, therapeutically effective amount of at least one of the glucosaminoglucan derivatives and excipients conventionally used in pharmaceutical compositions. The pharmaceutical compositions may be used in the form of phthials for intramuscular or endovenous injection, compresses, tablets, capsules, etc.

What is claimed is:

1. The method of preventing and treating cardiac infarct, cerebral infarct and venous thrombosis in a living subject which consists of administering to said living subject a modified heparin which exhibits low anticoagulant activity, low anti-Xa activity, said modified heparin being obtained by hydrolyzing the N-sulfate groups present in the original heparin to obtain a hydrolysed heparin containing less than 10% of said N-sulfate groups and then treating said modified heparin with succinyl anhydride or a compound capable of acting as a succinyl radical donor whereby said modified heparin contains more than 0.6 succinyl radical per disaccharide unit, in the amount of 0.5–300 mg/kg of body weight of said living subject.

* * * * *